(12) United States Patent
Nakamura et al.

(10) Patent No.: US 8,944,991 B2
(45) Date of Patent: Feb. 3, 2015

(54) INTER-ORGAN SPACER FOR USE IN ENDOSCOPIC SURGERY

(75) Inventors: Yoshiharu Nakamura, Tokyo (JP); Satoshi Matsumoto, Tokyo (JP); Toshiki Inoue, Tokyo (JP)

(73) Assignees: Nippon Medical School Foundation, Tokyo (JP); Hogy Medical Co., Ltd., Tokyo (JP)

( * ) Notice: Subject to any disclaimer, the term of this patent is extended or adjusted under 35 U.S.C. 154(b) by 39 days.

(21) Appl. No.: 12/810,997

(22) PCT Filed: Dec. 26, 2008

(86) PCT No.: PCT/JP2008/073859
§ 371 (c)(1),
(2), (4) Date: Jun. 28, 2010

(87) PCT Pub. No.: WO2009/084688
PCT Pub. Date: Jul. 9, 2009

(65) Prior Publication Data
US 2010/0286474 A1    Nov. 11, 2010

(30) Foreign Application Priority Data
Dec. 28, 2007 (JP) ................................. 2007-340837

(51) Int. Cl.
*A61F 2/00* (2006.01)
*A61F 13/00* (2006.01)
(Continued)

(52) U.S. Cl.
CPC ............. *A61B 17/02* (2013.01); *A61B 17/0218* (2013.01); *A61B 2019/4878* (2013.01); *A61B 2017/00898* (2013.01)
USPC .............................................. 600/37; 604/15

(58) Field of Classification Search
USPC ........ 600/37, 200, 204, 206, 208; 606/11–18, 606/114, 192–196; 604/358, 317; 246/36.11; 428/36.5
See application file for complete search history.

(56) References Cited

U.S. PATENT DOCUMENTS 3,961,629 A * 6/1976 Richter et al. ................ 604/369
4,098,728 A * 7/1978 Rosenblatt .................... 521/141
(Continued)

FOREIGN PATENT DOCUMENTS

| CN | 1094067 A | 10/1994 |
|----|-----------|---------|
| JP | 58131809 | 9/1983 |

(Continued)

OTHER PUBLICATIONS

Written Opinion of The International Searching Authority for PCT/JP2008/073859.
(Continued)

*Primary Examiner* — Charles A Marmor, II
*Assistant Examiner* — Eileen Foley
(74) *Attorney, Agent, or Firm* — Heslin Rothenberg Farley & Mesiti P.C.

(57) ABSTRACT

The invention provides a surgical device for endoscopic surgery having the function of temporarily storing liquid (a first function), the function of keeping a physical space for surgery and a sufficient endoscopic field (a second function), and the function of protecting organs (a third function), and an insertion device for inserting the surgical device into a body.
[Solving Means]
The surgical device for endoscopic surgery is an inter-organ spacer (10) including liquid holding means (1) formed of a porous soft material having the ability to temporarily store liquid and the ability to retain its shape. The insertion device for inserting the inter-organ spacer into a body includes a tubular holder capable of holding the inter-organ spacer for endoscopic surgery.

10 Claims, 4 Drawing Sheets

(51) Int. Cl.
*A61F 13/20* (2006.01)
*A61B 17/02* (2006.01)
*A61B 19/00* (2006.01)
*A61B 17/00* (2006.01)

(56) References Cited

U.S. PATENT DOCUMENTS

| | | | |
|---|---|---|---|
| 5,074,840 A * | 12/1991 | Yoon | 604/15 |
| 5,203,767 A * | 4/1993 | Cloyd | 604/11 |
| 5,362,294 A | 11/1994 | Seitzinger | |
| 5,437,651 A * | 8/1995 | Todd et al. | 604/313 |
| 5,453,078 A * | 9/1995 | Valentine et al. | 600/37 |
| 5,584,827 A * | 12/1996 | Korteweg et al. | 604/369 |
| 6,183,436 B1 * | 2/2001 | Korteweg et al. | 604/96.01 |
| 6,248,088 B1 * | 6/2001 | Yoon | 604/11 |
| 6,328,991 B1 * | 12/2001 | Myhling | 424/430 |
| 6,383,195 B1 | 5/2002 | Richard | |
| 6,841,586 B2 * | 1/2005 | Free et al. | 521/172 |
| 2001/0025155 A1 | 9/2001 | Yoon | |
| 2002/0107223 A1 | 8/2002 | Oster et al. | |
| 2002/0137988 A1 | 9/2002 | Shipp | |
| 2005/0267492 A1 * | 12/2005 | Poncet et al. | 606/114 |
| 2007/0118074 A1 * | 5/2007 | Dario et al. | 604/57 |
| 2007/0135907 A1 * | 6/2007 | Wilson et al. | 623/1.44 |
| 2008/0161638 A1 * | 7/2008 | Taylor et al. | 600/16 |

FOREIGN PATENT DOCUMENTS

| | | |
|---|---|---|
| JP | 8164162 A | 6/1996 |
| JP | 2002325773 | 12/2002 |
| JP | 2005296562 A | 10/2005 |
| JP | 2006519633 A | 8/2006 |
| RU | 2285515 C2 | 10/2006 |
| WO | 02/49565 A2 | 6/2002 |

OTHER PUBLICATIONS

International Search Report for PCT/JP2008/073859, dated Jan. 13, 2009.
English translation of Russian Office Action, Russian Application No. 2010131619/14(044728), Date of filing of the Application Dec. 26, 2008, PCT Application No. JP2008/073859 filed Dec. 26, 2008.
Comeau, Perry J., "The Blood Loss Analyzer—A New Way To Estimate Blood Loss", *Journal of the American Association of Nurse Anesthetists*, pp. 81-84 (1983).
Written Opinion of The International Searching Authority for PCT/JP2008/073859, Aug. 4, 2010 (see attached).

* cited by examiner

INTER-ORGAN SPACER FOR USE IN ENDOSCOPIC SURGERY

CROSS REFERENCE TO RELATED APPLICATIONS

This application is a national phase filing under 35 U.S.C. §371 of PCT International Application PCT/JP2008/073859, filed Dec. 26, 2008, and published under PCT Article 21(2) in Japanese as WO 2009/084688 A1 on Jul. 9, 2009. PCT/JP2008/073859 claims priority from Japanese application No. 2007-340837 filed on Dec. 28, 2007. The entire contents of each of the prior applications are incorporated herein by reference.

TECHNICAL FIELD

The present invention relates to an inter-organ spacer for use in endoscopic surgery and an insertion device for inserting the spacer into a body.

BACKGROUND ART

Endoscopic surgery includes thoracic or abdominal surgery performed under the monitoring of images from an endoscope (e.g., thoracoscope or laparoscope) inserted in a thoracic or abdominal cavity. In laparoscopic surgery, for example, unlike traditional abdominal surgery (laparotomy), incisions in the abdomen are not large, and operations are performed using several necessary small-diameter (about 5 to 15 mm) tubes (trocars) which are inserted in the abdomen and through which a laparoscope and small forceps (an instrument used for grasping or holding an organ) developed for endoscopic surgery are put in and out. In order to perform the surgery under careful observation of the abdominal cavity, carbon dioxide gas is also insufflated into the abdominal cavity to inflate the abdomen (called pneumoperitoneum) or to elevate the abdominal wall.

As compared with laparotomy, endoscopic surgery has advantages such as:

small incision, cosmetically good result, and less pain after surgery; and the effect of magnification by laparoscope, which makes possible delicate techniques with less bleeding.

Thanks to the low invasiveness, endoscopic surgery has made remarkable progress.

However, endoscopic surgery has the following problems.

Once bleeding occurs, the endoscopic field is degraded, and hemostasis is more difficult than in laparotomy.

Carbon dioxide gas is usually injected into the abdominal cavity for pneumoperitoneum. Therefore, when exudates and blood are sucked during surgery, abdominal gas ($CO_2$) is simultaneously sucked, so that the endoscopic field can be difficult to maintain, which makes suction more difficult than in laparotomy.

In two-dimensional monitoring, it is difficult to monitor organs in the deep field, which creates the risk of damage to organs.

Organs cannot be directly touched by hand and fingers, and operations are performed using hard forceps, which makes it difficult to protectively treat organs.

These problems are common to all endoscopic operations of abdominal organs, which include operations in the field of not only digestive surgery but also gynecology and urology.

These problems, which are not significant for usual laparotomy, are unique to endoscopic surgery. In usual laparotomy, for example, bleeding can be stopped by holding gauze or the like directly to the bleeding part, and it is easy to replace the gauze with new gauze one after another. In usual laparotomy, pneumoperitoneum is not necessary, and organs can be directly observed with no monitor, and therefore, a sufficient visual field is ensured. In laparotomy, organs can be treated directly by hand and fingers, so that protective exclusion or protection of organs is possible. As described above, the problems with endoscopic surgery are not significant for laparotomy with a long history, and therefore, there is no medical device capable of solving the problems found in the medical devices for laparotomy.

Examples of organ exclusion or traction instruments for endoscopic surgery include a triangle retractor (Stemmer, Germany) and a retractor (e.g., manufactured by MIZUHO Co., ltd. or Heiwa Iryo Kikai Co., Ltd.). When these instruments are used, however, at least one trocar is occupied. In addition, at present, these instruments are used only in very restricted situations.

X-ray contrast thread-containing gauze for laparotomy is also used for the absorption of blood and exudates in endoscopic surgery. In endoscopic surgery, however, it is difficult to frequently put gauze in and out through a trocar, and the replacement with new gauze is not easy, in contrast to laparotomy. In endoscopic surgery, therefore, blood and the like once absorbed in gauze is generally sucked through a suction tube, which is additionally inserted through a trocar, and the gauze is generally used again for the absorption of blood and the like. However, gauze is thin and relatively weak and therefore creates the risk of damage to an organ from the tip of a suction tube in the process of suction through the suction tube. In addition, gauze may adhere to the organ when dried, and the adhering gauze may cause damage to the organ when peeled off. It is also difficult to appropriately fold gauze in the abdominal cavity, which causes the disadvantage that it is difficult to protectively wrap or press an organ as in laparotomy.

DISCLOSURE OF THE INVENTION

Problems to be Solved by the Invention

Under the circumstances, the present inventors have made investigations to provide a completely new surgical device for solving the unique problems with endoscopic surgery, which have not been significant to date for laparotomy with a long history, and as a result, have completed the invention. The functions required of such a surgical device include, but are not limited to, the function of temporarily storing liquid for suction and removal of blood and exudates during endoscopic surgery (a first function), the function of keeping a physical space for surgery and a sufficient endoscopic field (a second function), and the function of protecting organs (a third function). An object of the invention is to provide a completely new endoscopic surgery device having these functions.

As is evident from the object of the invention, the surgical device of the invention is intended to be used in the body only during endoscopic surgery and intended to be taken out of the body when the object of surgery is achieved. Therefore, the technical field pertinent to the invention completely differs from that of products intended to be left in the body after surgery, such as a wound covering material and an anti-adhesion material (see, for example, Japanese Patent Application National Publication No. 2006-519633).

Means for Solving the Problems

The above problems can be solved using the inter-organ spacer of the invention for endoscopic surgery, which includes liquid holding means formed of a porous soft material having the ability to temporarily store liquid and the ability to retain shape. The porous soft material is preferably soft polyurethane foam.

The invention is also directed to an insertion device for insertion of the inter-organ spacer into the body, which includes a tubular holder capable of holding the inter-organ spacer for endoscopic surgery. In a preferred aspect of the invention, the insertion device may further include ejecting means capable of being inserted from one end of the tubular holder and capable of ejecting the inter-organ spacer in the tubular holder from the other end of the tubular holder. In another preferred aspect of the invention, the insertion device may further include pulling means capable of pulling the inter-organ spacer into the tubular holder. In a further preferred aspect of the invention, the insertion device may further include a funnel portion capable of being provided at one end of the tubular holder. The invention is also directed to an endoscopic surgery kit including the inter-organ spacer for endoscopic surgery and the insertion device.

As used herein, the term "endoscopic surgery" is intended to include thoracic or abdominal surgery performed under the monitoring of images from an endoscope (e.g., thoracoscope or laparoscope) inserted in the thoracic or abdominal cavity. In laparoscopic surgery, for example, unlike traditional abdominal surgery, incisions in the abdomen are not large, and operations are performed using several necessary small-diameter (about 5 to 15 mm) tubes (trocars) which are inserted in the abdomen and through which a laparoscope and small forceps (an instrument used for grasping or holding an organ) developed for endoscopic surgery are put in and out. In a stomach or intestine operation, small incisions of about 5 cm are often formed for excision, removal or anastomosis (joining) of the organs, and such an operation is called laparoscope-assisted surgery, which is also encompassed by the endoscopic surgery as used herein.

Effects of the Invention

Use of the inter-organ spacer of the invention simultaneously solves various problems specific to endoscopic surgery. The advantages obtained include:
(1) prevention of bleeding-induced hindrance in the endoscopic field,
(2) buffering of the force pressing organs or tissues,
(3) prevention of organ damage caused by the transfer of heat or oscillating waves and prevention of secondary damage when using an automatic suturing machine,
(4) pressure to stop unexpected bleeding, and
(5) suction of exudates (mainly blood).
Effect (1)
In endoscopic surgery, even a small amount of bleeding may interfere with the endoscopic field to impede smooth operation. However, when the inter-organ spacer of the invention is inserted, blood or exudates, such as bile or intestinal fluid, can be immediately absorbed into the liquid holding means, preventing it from diffusing to the surroundings.
Effect (2)
In endoscopic surgery, the target organ or tissue is subjected to exclusion through the use of instruments, such as forceps, by remote control. This is because the target organ or tissue cannot be protectively pressed (subjected to exclusion) with the hand or fingers. In this process, the force may often be concentrated at one point, causing damage to the organ or tissue. The inter-organ spacer of the invention may be placed between the forceps and the organ or tissue to dissipate the force so that it is no longer concentrated, reducing the risk of damage.
Effect (3)
In endoscopic surgery, an electric cautery or ultrasonic coagulation shears are generally used to peel, cut or separate organs or tissues. In this process, however, unnecessary heat or oscillating waves may be transmitted to critical organs or tissues to create the risk of unexpected damage. The inter-organ spacer of the invention may be interposed between the organ or tissue to be separated and the electric cautery or ultrasonic coagulation shears or placed before the critical organ so that unnecessary heat or oscillating waves are not transmitted, preventing secondary damage. In endoscopic surgery, an automatic suturing machine is often used to cut and separate organs and tissues. In this case, adjacent organs or tissues can become affected and damaged. However, when the inter-organ spacer of the invention is interposed, secondary damage can be avoided.
Effect (4)
The basic technique to stop bleeding is pressure hemostasis. The insertion of the inter-organ spacer of the invention makes it possible to quickly perform pressure hemostasis to stop unexpected bleeding.
Effect (5)
In endoscopic surgery, accumulated exudates are usually sucked through a suction tube. In some cases, however, surrounding tissues may also be sucked into the suction tube, impeding smooth suction of the exudates. Therefore, if there is excessive bleeding, the endoscopic field may be suddenly degraded so that it becomes necessary to abandon the endoscopic operation. Using the inter-organ spacer of the invention, exudates can be immediately absorbed and then sucked through the liquid holding means, so that the exudates can be efficiently removed.

REFERENCE SIGNS LIST

10: inter-organ spacer; 1: main sponge body; 2: grasping cord; 3: through hole; 20: introducer-type insertion device; 21: tubular holder; 22: ejecting means; 30: extractor-type insertion device; 31: tubular holder; 32: pulling means; 40: extractor-type insertion device; 41: tubular holder; 42: funnel portion Best Mode for Carrying Out the Invention In the invention, the inter-organ spacer for use in endoscopic surgery includes, at minimum, liquid holding means formed of a porous soft material having the ability to temporarily store liquid and the ability to retain its shape. If desired, it may further include, for example, a gripping cord (preferably one that contains an X-ray contrast agent) that may be provided on the surface of the liquid holding means, or an X-ray contrast agent in the inside of the liquid holding means. The liquid holding means, which is a main part of the inter-organ spacer of the invention, has the dual functions of temporarily storing liquid and of maintaining a space to protect the organs.

In the invention, the porous soft material used to form the liquid holding means may be of any type, as long as it has, at minimum, the ability to temporarily store liquid and the ability to retain its shape. In the preferred mode, it also has flexibility.

As used herein, the term "the ability to temporarily store liquid" means that the material has (1) an ability to absorb liquid (liquid absorbency) such that it can absorb blood or exudates during surgery, (2) an ability to hold liquid (liquid holding ability) such that it can sufficiently hold the absorbed blood or the like even when an external action (such as transfer or contact with organs during surgery) is applied to the liquid holding means during surgery, and (3) an ability to release liquid (liquid releasing ability or deliquoring ability) such that the blood or the like absorbed by the liquid holding means can be discharged from the liquid holding means by suction or the like.

For example, the liquid absorbency may be evaluated by the ability to absorb liquid for the own weight or by the liquid absorption rate when a predetermined amount of a solution is absorbed. The liquid absorbency of the porous soft material for use in the invention is preferably from 100% to 5,000% of its own weight (1 to 50 times its own weight), when the ability to absorb liquid for its own weight is used as an index. If it is 100% or more of the own weight, there is the advantage that the effect of absorbing liquid in an amount of the volume or more can be produced, so that when the spongy material is placed in the body, such liquid as body fluid can be prevented from interfering with the space for surgery or overflowing out of the body. If it is more than 5,000% of the own weight, the spongy material may be reduced in physical strength. The lower limit of the liquid absorbency is more preferably 150%, even more preferably 200%, and particularly preferably 300% of the own weight. The upper limit is more preferably 3,000%, even more preferably 2,000%, and particularly preferably 1,000% of the own weight.

The liquid absorbency is the value measured by the following procedure. (1) The weight (Wd) of the test object (such as a sponge) is measured before it is immersed in artificial blood. (2) It is immersed in artificial blood for 3 minutes (the whole of the sponge is immersed in the liquid so that the liquid can be absorbed from the largest possible area of the whole surface of the sponge), and then it is placed on a wire mesh for 30 seconds so that excess artificial blood is allowed to drip naturally. Thereafter, the weight (Ww) of the test object after the absorption is measured. (3) The liquid absorbency (%) is calculated by dividing the increase in the weight by the weight before the absorption according to the following formula: $(Ww-Wd) \div Wd \times 100(\%)$.

Alternatively, when the liquid absorption rate in the case where a predetermined amount of a solution is absorbed is used as an index, the liquid absorbency of the porous soft material for use in the invention is preferably from 40% to 100%. The lower limit of the liquid absorbency is more preferably 60%, even more preferably 80%, still more preferably 85%, and particularly preferably 90%. This absorbency is the value measured by the following procedure. The sample (in the shape of a rectangular parallelepiped of 50 mm×50 mm×20 mm) is allowed to absorb a sufficient amount of artificial blood, and then it is sufficiently wrung. The lid of a disposable Petri dish with a diameter of 9 cm is turned upside down and placed on a table, and 20 mL of artificial blood is placed therein. The sample wrung sufficiently is placed therein, and the sample is pressed five times with the bottom surface of the Petri dish. In this process, the sample is pressed until it is no longer compressible, and the pressing is performed about once per second. The sample is taken out, and the amount (V in units of mL) of the artificial blood left in the lid of the Petri dish is measured. The liquid absorbency is calculated from the following formula: $(20\ mL-V)/20\ mL \times 100(\%)$.

The liquid holding ability of the porous soft material for use in the invention is preferably from 90 to 100%, more preferably from 92 to 100%, even more preferably from 94 to 100%, and still more preferably from 97 to 100%. The liquid holding ability is the value measured by the following procedure. (1) The weight (Wd) of the test object before liquid absorption is measured. (2) The test object is allowed to absorb a sufficient amount of artificial blood, and the weight (Ww) of the liquid-containing object is measured. (3) The liquid-containing object is placed on a plate, and the plate is allowed to stand for 3 minutes, while being tilted at 45°. Thereafter, the weight ($W_3$) of the object is measured. (4) The liquid holding ability (%) is defined as the value calculated from the following formula: $(W_3-Wd) \div (Ww-Wd) \times 100(\%)$.

The liquid releasing ability of the porous soft material for use in the invention is preferably from 10 to 100%, more preferably from 15 to 100%, even more preferably from 20 to 100%, still more preferably from 40 to 100%, yet more preferably from 60 to 100%, and further more preferably from 65 to 100%. In the invention, a porous soft material with a liquid releasing ability of 80 to 100% or 85 to 100% may also be used.

The liquid releasing ability is the value measured by the following procedure. (1) The weight (Wd) of the test object before liquid absorption is measured. (2) The test object is allowed to absorb a sufficient amount of artificial blood, and the weight (Ww) of the liquid-containing object is measured. (3) The liquid-containing object is placed on a plate, and the weight (Ws) of the object is measured, after the liquid is sucked for 1 minute at a suction power of −600 to −650 mmHg (−80 to −85 kPa), while a suction tip is held to the center of the object. (4) The liquid releasing ability (%) is defined as the value calculated from the following formula: $(Ww-Ws) \div (Ww-Wd) \times 100(\%)$.

As used herein, the term "low liquid releasing ability" means that the liquid releasing ability measured by the method described above is less than 40%, and the term "high liquid releasing ability" means that it is 40% or more.

As used herein, the term "the ability to retain shape" means such properties that even when the inter-organ spacer of the invention is inserted into the body and then loaded with various external pressures as expected during endoscopic surgery, its shape can be substantially retained. Examples of the external pressures include pressures applied from a suction tube during liquid-discharging operation, pressures applied during transfer of the inter-organ spacer, pressures applied in the process of keeping a space for surgery, and pressures applied in the process of protecting organs.

For example, the ability to retain shape may be evaluated using compressive residual strain.

The porous soft material for use in the invention preferably has a compressive residual strain of 10% or less, and more preferably 5% or less. The compressive residual strain is preferably as low as possible, and therefore, the lower limit is 0%. If it is more than 10% (preferably 5%), the surface area of the spongy material may be reduced, so that the water absorbing properties and the flexibility may be reduced.

As used herein, the term "compressive residual strain" means the value measured according to JIS K 6400 (1997). The measurement is briefly described below. The thickness ($t_0$) of the center of the test piece (50 mm×50 mm×20 mm) is measured in increments of 0.1 mm with a vernier caliper, while its form is not changed. Subsequently, the thickness of the test piece is reduced to 50% using two compression plates. Within at most 15 minutes, the test piece being compressed is placed in a thermostatic chamber at a temperature of 70±1° C. and heated for 22 hours. The test piece is taken out of the thermostatic chamber, separated from the compression plates within 1 minute, and placed on a low thermal conductivity material such as a wood material. The test piece is allowed to stand at a temperature of 23±2° C. and a relative humidity of 50±5% (in a chamber controlled for 16 hours or more) for 30 minutes to be restored, and then the thickness ($t_1$) of the same portion is measured in increments of 0.1 mm. The compressive residual strain (%) is defined as the value calculated from the following formula: $(t_0-t_1)\div t_0\times 100(\%)$, wherein $t_0$ is the thickness before the compression, and $t_1$ is the thickness after the compression.

As used herein, the term "flexibility" means such surface properties that the material does no damage to organs when brought into contact with the organs. For example, the flexibility may be evaluated according to JIS K 6400 or evaluated using the hardness or impact resilience measured according to it.

The porous soft material for use in the invention preferably has a hardness of 10 to 200 N. The lower limit of the hardness is more preferably 15 N, even more preferably 20 N, and particularly preferably 25 N. The upper limit of the hardness is more preferably 150 N, and even more preferably 100 N.

As used herein, the term "hardness" means the value measured by the method described in Example 5 below, which is performed according to JIS K 6400 (1997). Specifically, the test sample (a laminate of two pieces of 80×80×20 mm) is placed on the mount of a tester, and a pressing plate (33.7 mm in diameter) is placed on the upper surface of the sample piece so that a load of 0.2 N is applied, when the thickness of the sample is read in increments of 0.1 mm as the initial thickness. The pressing plate is then pushed in 10 mm at a rate of 100±20 mm/minute, and immediately thereafter, the load is removed. Once again, the pressing plate is pushed in 30 mm at a rate of 100±20 mm/minute, and 20 seconds after the stop, the load is recorded.

The porous soft material for use in the invention preferably has an impact resilience of 10 to 100. The lower limit is more preferably 20, and even more preferably 30. As used herein, the term "impact resilience" means the value measured by the method described in Example 6 below, which is performed according to JIS K 6400 (1997). Specifically, a ⅝ normal steel ball specified in JIS B 1501 is placed 476 mm above the test sample (a laminate of two pieces of 80×80×20 mm) and allowed to freely fall. The uppermost level of the bounding steel ball is measured. In the quantification, the positions 16 mm and 476 mm above the sample piece are normalized as 0 and 100, respectively.

In addition to the ability to temporarily store liquid, the ability to retain shape and flexibility described above, if desired, the porous soft material for use in the invention preferably has deformability, sterilization resistance, non-sticking properties, durability, moderate swelling properties, or the ability to indirectly absorb liquid. The inter-organ spacer of the invention is a surgical tool, which is intended to be used in the body only during endoscopic surgery and to be removed from the body after the achievement of the object of surgery. Therefore, the porous soft material for use in the invention does not have to be biodegradable. In view of strength, cost or the like, it is preferably rather non-biodegradable.

As used herein, the term "deformability" means such properties that when inserted into the body through a trocar, the material can be deformed into a shape capable of passing through the trocar. The deformability is not essential, when the material is of such shape and size that it can pass through a trocar without changing its shape. The deformability and the ability to retain shape are seemingly contradictory to each other. As described above, however, the ability to retain shape as used herein means such properties that when various external pressures as expected are applied during endoscopic surgery, the shape can be substantially retained, while the deformability as used herein means that for the passage through a trocar, the shape can be changed as described above by applying a very high load (specifically, a load extremely higher than the external pressure expected during endoscopic surgery). Therefore, the deformability and the ability to retain shape are not contradictory to each other.

When the material has sterilization resistance (such as heat resistance, chemical resistance, or UV resistance), the product can be provided in a sterile state. When the material also has non-sticking properties, sticking to organs can be prevented.

The material having sufficient durability does not tear, even when part of it is grasped with a forceps or the like, or the material having sufficient durability can be prevented from being dissolved or collapsed in the body and from remaining in the body, so that it can be safely used in endoscopic surgery. For example, the durability may be evaluated using tensile strength. The porous soft material for use in the invention preferably has a tensile strength of 5 N or more, more preferably 8 N or more, even more preferably 10 N or more, still more preferably 20 N or more, and yet more preferably 23 N or more. The upper limit of the tensile strength is preferably 200 N, more preferably 150 N, even more preferably 100 N, and particularly preferably 50 N.

As used herein, the term "tensile strength" means the value measured according to JIS K 6400-5 (2004). The outline is as follows. A 1 cm-thick No. 2 test piece is prepared. While the test piece is pulled at a rate of 500 mm/minute, the maximum load is measured until the test piece is ruptured.

The porous soft material for use in the invention preferably has a degree of swelling of 50% to 150%, more preferably 90% to 110%, and even more preferably 95% to 105%. As used herein, the term "degree of swelling" means the value measured by the method described in Example 8 below. Specifically, 50 mL of artificial blood is put in a 100 mL volume beaker. A sample whose dimensions (length, width and height) have been previously measured (about 20 mm×20 mm×10 mm) is gently dropped into the artificial blood-containing beaker and allowed to stand for 3 minutes. Thereafter, the sample is gently taken out with tweezers and placed on a wire mesh for 30 seconds so that the artificial blood is allowed to drip. Thereafter, the dimensions of the sample are measured again. The degree of swelling (%) is defined as the value calculated from the following formula: (Vw/Vd)×100(%), wherein Vw is the volume of the sample after the liquid absorption, and Vd is the volume of the sample before the liquid absorption.

As used herein, the term "the ability to indirectly absorb liquid" means the performance evaluated by the method described in Example 9 below. Specifically, the sample (in the shape of a rectangular parallelepiped of 80 mm×80 mm×20 mm) is allowed to stand in a vessel of 12 cm×23 cm×5 cm containing 50 mL of artificial blood, and the upper surface of the sample is repeatedly pushed, so that a sufficient amount of artificial blood is absorbed in the sample. After it is confirmed that a sufficient amount of artificial blood not absorbed is left around the sample, the top of a suction tip is held to the center of the sample. The artificial blood is sucked under a reduced pressure of −600 to −650 mmHg (−80 to −85 kPa), while the suction tip is pushed in. It is checked whether or not the whole amount of the artificial blood in and around the sample is removed after the suction for a sufficient period of time. The suction time is set to 1 minute. When the artificial blood around the sample is removed in 1 minute or less, the sample is determined to have the ability to indirectly absorb liquid. When some artificial blood is not removed and left around the sample even after the 1 minute suction, the sample is determined not to have the ability to indirectly absorb liquid. When the porous soft material shows the ability to indirectly absorb liquid, the suction removal object such as blood, exudate such as bile or intestinal fluid, or a saline used to wash organs does not need to be sucked directly, and exudate can be indirectly removed through the liquid holding means, so that the risk of damaging tissues and so on can be avoided.

The porous soft material for use in the invention can have various properties as described above. Therefore, various problems specific to endoscopic surgery as described above can be solved using the porous soft material. Among these properties, only a high level of liquid absorbency and liquid holding ability are not enough for some inter-organ spacers for use in endoscopic surgery, and the liquid releasing ability, the ability to indirectly absorb liquid, and the strength (such as tensile strength) are particularly important.

Examples of the porous soft material for use in the invention include various sponges (soft foams) available for medical use. More specifically, for example, polyurethane (polyurethane with low liquid releasing ability or high liquid releasing ability), polyvinyl alcohol, cellulose, polyethylene, or the like may be used, as long as it has various properties as described above, and polyurethane is particularly preferred.

Considering all of the various properties described above (particularly, the liquid releasing ability, the strength, the ability to indirectly absorb liquid, and so on), the porous soft material for use in the invention is preferably polyurethane with high liquid releasing ability. Examples thereof include the polyurethane materials with high liquid releasing ability used in the examples described below (such as samples B, C, D, E, and b). Further taking the tensile strength into account, samples B and E are preferred among these polyurethane materials with high liquid releasing ability. On the other hand, samples B, C and D are preferred in view of the ability to indirectly absorb liquid. From all of these points of view, therefore, sample B is most preferred.

Table 1 shows various properties of polyurethane materials with high liquid releasing ability, which may be used in the invention, together with those of general polyurethane materials, which may also be used in the invention. In Table 1, column I indicates preferred ranges common to samples B, C, D, E, and b, column II indicates more preferred ranges common to samples B, C, D, and E, and column III indicates even more preferred ranges common to samples B and E. Column IV concerns general polyurethane materials.

TABLE 1

| Properties | I | II | III | IV |
|---|---|---|---|---|
| Density (kg/m³) | 10-40 | 10-40 | 25-40 | 10-90 |
| Number of cells (cells/25 mm) | 20-70 | 20-70 | 35-70 | 15-90 |
| Elongation (%) | 50-400 | 50-400 | 150-400 | 40-500 |
| Ability to temporarily store liquid | | | | |
| Liquid absorbency (%) | 80-100 | 80-100 | 85-100 | 70-100 |
| Liquid holding ability (%) | 90-100 | 90-100 | 98-100 | 80-100 |
| Liquid releasing ability (%) | 40-100 | 40-100 | 40-100 | 15-100 |
| Ability to retain shape | | | | |
| Compressive residual strain (%) | 0.5-7 | 0.5-7 | 0.5-4 | 0.5-10 |
| Flexibility | | | | |
| Hardness (N) | 10-30 | 10-30 | 15-30 | 10-50 |
| Impact resilience | 35-70 | 35-70 | 35-55 | 20-80 |
| Durability | | | | |
| Tensile strength (N) | 5-40 | 8-40 | 15-40 | 5-50 |
| Degree of swelling (%) | 95-105 | 95-105 | 98-102 | 90-110 |

Also, as shown in the examples below, polyurethane material A with low liquid releasing ability is superior to polyurethane material b in liquid absorbency, tensile strength and so on. As compared with polyvinyl alcohol for use in a pad for organ exclusion, polyurethane with low liquid releasing ability is superior in flexibility (e.g., hardness or impact resilience), compressive residual strain or the like. As compared with cellulose for use in a pad for organ exclusion (such as Opesponge X (Hakujuji Co., Ltd.)), polyurethane with low liquid releasing ability is superior in mechanical strength. On the other hand, polyurethane with high liquid releasing ability is superior in liquid releasing ability.

Figure 1:
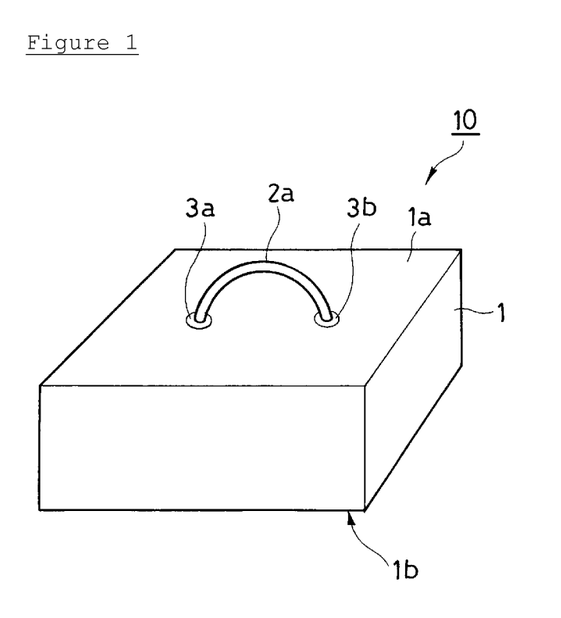
FIG. 1 is a perspective view schematically showing an aspect of an inter-organ spacer of the invention.
Figure 2:
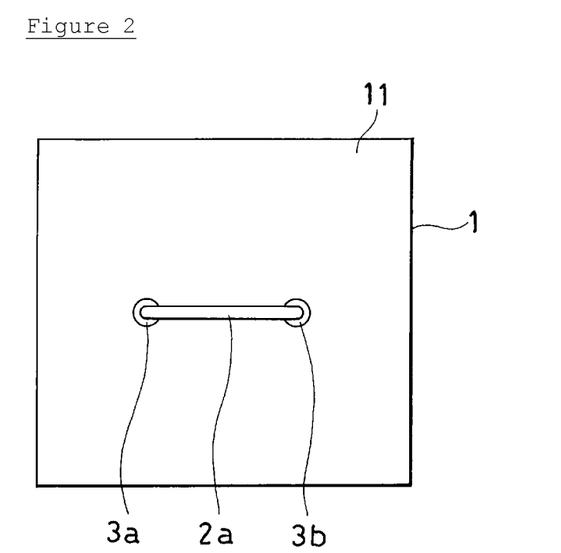
FIG. 2 is a schematic plan view of the inter-organ spacer shown in FIG. 1.
Figure 3:
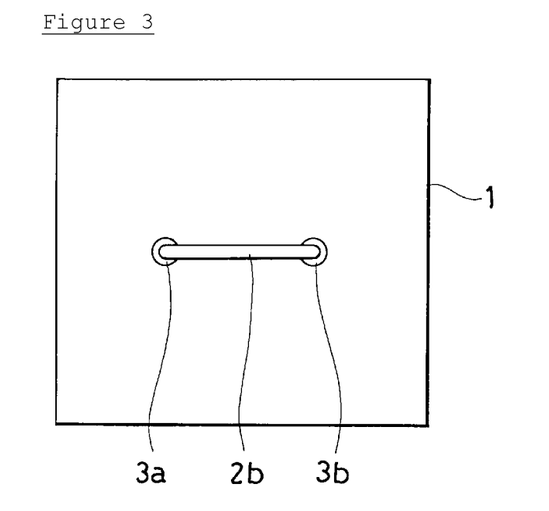
FIG. 3 is a schematic bottom view of the inter-organ spacer shown in FIG. 1.
Figure 4:
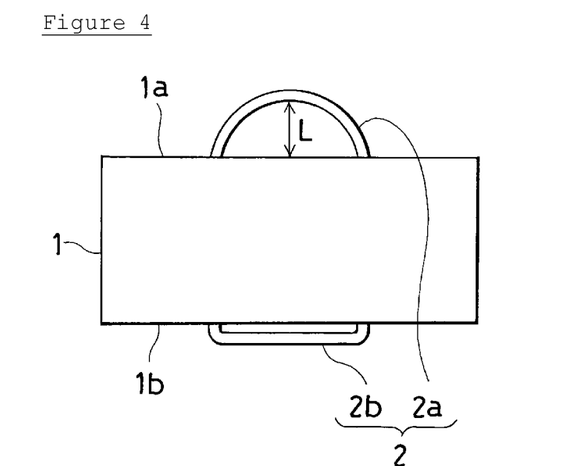
FIG. 4 is a schematic side view of the inter-organ spacer shown in FIG. 1.

FIG. 1 schematically shows an aspect of the inter-organ spacer of the invention. FIGS. 2 to 4 show plan, bottom and side views of the inter-organ spacer shown in FIG. 1, respectively. An inter-organ spacer 10 shown in FIG. 1 includes a main sponge body 1 to function as liquid holding means and a gripping cord 2. The main sponge body 1 is in the shape of a quadrangular prism having a square top face 1a and a square bottom face 1b, in which a pair of through holes 3a and 3b is formed between the top face 1a and the bottom face 1b. The cord 2 contains an X-ray contrast thread and forms a closed circular structure that links a space in the vicinity of the top face 1a of the main sponge body 1, the inside of one through hole 3a, a space in the vicinity of the bottom face 1b, and the inside of the other through hole 3b together in this order.

The cord 2 may be fixed to the main sponge body 1 in the inside of the through holes 3a and 3b or may not be fixed thereto. When the cord 2 is fixed to the main sponge body 1, each of the length of a substantially circular arc portion 2a protruding from the top face 1a and the length of a substantially linear portion 2b protruding from the bottom face 1b does not change during use. When the cord 2 is not fixed to the main sponge body 1, each length may be changed before and/or during use. The length of the cord provided may be controlled so that only the portion (the substantially circular arc portion 2a) protruding from one face (the top face 1a) can function as a grip portion (see FIG. 4). Alternatively, the portions protruding from both faces (the top and bottom faces 1a and 1b), respectively, may be provided so as to function as grip portions, respectively.

When used for protective exclusion with no damage to organs during endoscopic surgery, the main sponge body 1 can function as a spacer for keeping the space necessary for the surgery. In endoscopic surgery, it can also function as a protective member for protecting organs and as a material for absorbing blood and exudates.

The liquid holding means (e.g., the main sponge body) of the inter-organ spacer of the invention may be of any size, as long as it can be inserted in a compressed, wound or folded form or as it is, through an incision in the body surface during endoscopic surgery. In endoscopic surgery, typical incisions are 40 mm at the maximum, generally from 5 to 12 mm, and 2 mm at the minimum. Typical trocars generally have a diameter of 2 to 30 mm, preferably 5 to 12 mm. The size of the liquid holding means may be appropriately determined depending on the incision size or the trocar diameter. For example, the thickness may generally be selected from the range of 0.5 to 10 cm. When it is in the form of a rectangular parallelepiped, its size may be selected from the range of 5 cm×5 cm×0.5 cm to 10 cm×10 cm×10 cm. The inter-organ spacer of the invention may be removed from the body via an incision or a trocar, while it is compressed, as it is, or after it is cut into small pieces by means of an electric cautery.

The gripping cord, which may be optionally attached to the inter-organ spacer of the invention, may be made of any material that makes it possible to grasp the cord with a forceps so that the main sponge body can be freely moved during surgery. For example, fibers, soft plastics, hard plastics, metals, or the like may be used. When a hard material capable of retaining the grip shape is used, the gripping cord can be easily gripped, and the main sponge body can be smoothly moved. When such a soft material that the grip shape cannot be retained is used, the risk of damage to organs can be reduced.

In the inter-organ spacer of the invention, the gripping cord may have any length that makes it possible to grasp the cord with a forceps so that the liquid holding means can be moved during endoscopic surgery. Preferably, the distance from the surface of the liquid holding means (the length L in FIG. 4) is from 1 mm to 100 mm, more preferably from 10 mm to 50 mm.

In the invention, the gripping cord may be joined to the liquid holding means by any joining method that makes it possible to provide the surface of the liquid holding means with the gripping cord so that the liquid holding means can be moved using the gripping cord. Examples of the joining methods include a joining method including forming one or more through holes in the liquid holding means, passing the cord through the hole(s), and then forming the cord into a closed loop; a joining method including dividing the liquid holding means into two parts and sandwiching the cord therebetween; and a method of directly joining the cord to one or more surfaces of the liquid holding means using bonding means (such as an adhesive tape, an adhesive or heat seal). A joining method including forming through holes in the main sponge body, passing the cord through the holes, and then forming the cord into a closed loop is preferred, because it does not need to use any adhesive or the like. The cord may be passed once, twice or more to form a single-, double- or multi-ply gripping cord. For example, a double- or multi-ply cord can increase the intensity of the X-ray photographic image or can be expected in increasing the reliability of the inter-organ spacer (can increase the contact area between the gripping cord and the liquid holding means so that the risk of tearing of the liquid holding means can be reduced). In the case of a double- or multi-ply cord, the double-ply cord is particularly preferred in view of the above effect and cost.

In the inter-organ spacer of the invention, the gripping cord may contain an X-ray contrast agent. For example, barium sulfate or a mixture of barium sulfate and polyamide, polypropylene or synthetic rubber may be used as the X-ray contrast agent. Examples of methods of allowing the gripping cord to contain an X-ray contrast agent include methods of producing the gripping cord with an X-ray contrast thread(s) and methods of sealing an X-ray contrast thread(s) into the gripping cord. Examples of methods of adding the function of an X-ray contrast agent to the inter-organ spacer of the invention include, but are not limited to, using the gripping cord, a method including mixing an X-ray contrast agent into a sponge material and then forming a sponge, a method of injecting an X-ray contrast agent into the sponge, a method of inserting an X-ray contrast agent-containing cord, rod or sheet into the sponge, a method of attaching an X-ray contrast agent-containing tag, a method of attaching X-ray contrast agent-mixed or coated staples, and a method of sewing, into the sponge, an X-ray contrast thread(s) prepared by the same method as described above for the gripping cord.

Figure 5:
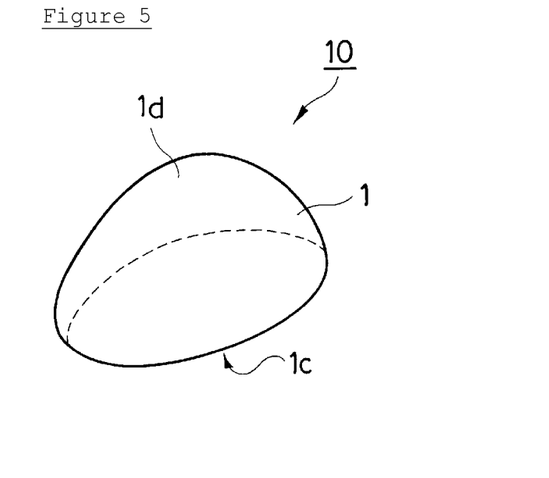
FIG. 5 is a perspective view schematically showing another aspect of the inter-organ spacer of the invention.

The liquid holding means (e.g., the main sponge body) of the inter-organ spacer of the invention may be in any shape that makes it possible to use the spacer for organ exclusion in endoscopic surgery. Examples of such a shape include a prismatic shape whose top and bottom faces are each a polygon (such as a triangle, square, rectangle, parallelogram (preferably rhombus), trapezoid, or regular hexagon); a pyramidal shape whose bottom face is a polygon (such as a triangle, square, rectangle, parallelogram (preferably rhombus), trapezoid, or regular hexagon); a truncated pyramid shape or a bipyramid shape (a solid formed by placing the bottom faces of two pyramids in contact with each other); a cylindrical shape whose top and bottom faces are each a circle or an ellipse; a conical shape whose bottom face is a circle or an ellipse, a truncated cone shape or a bicone shape (a solid formed by placing the bottom faces of two cones into contact with each other); a partially cylindrical shape whose top and bottom faces are each a partial circle or a partial ellipse (such as a semi-circle, a semi-ellipse, a sector, or a circular segment (a figure formed by an arc and a chord)), a partially conical shape whose bottom face is a partial circle or a partial ellipse (such as a semi-circle, a semi-ellipse, a sector, or a circular segment (a figure formed by an arc and a chord)), a truncated partially-conical shape or a partial bicone shape; a sphere or a partial shape thereof (such as a hemisphere, a spherical crown (various solids formed by cutting a sphere with a single plane), a spherical zone (a solid formed by cutting a sphere with two parallel planes and formed between the two planes), an oval sphere (or oval shape) or a partial shape thereof; and a regular octahedron (composed of eight equilateral triangles), a regular dodecahedron (composed of 12 regular pentagons), or a regular icosahedron (composed of twenty equilateral triangles). A shape incapable of forming a necessary space between organs, such as a thin sheet-like shape, a cord-like shape, or a belt-like shape is not preferred as the shape of the inter-organ spacer of the invention. A partial shape of an oval sphere (such as one of two solids obtained by equally dividing an oval sphere by a plane) as shown in FIG. 5 or a hemisphere is preferred, because it is highly stable when placed with the flat side (1c in FIG. 5) down and provides a curved surface (1d in FIG. 5) to be in contact with organs.

The inter-organ spacer of the invention may be inserted into the body through an incision in the body surface (preferably through a trocar), in a compressed, wound or folded state, in a deformed state, or as it is. More specifically, examples include a method of inserting it, into the body, in a compressed state formed by vacuum packing in a soft resin bag or a method of taking it out of the bag and inserting it into the body, a method of using the insertion device of the invention to insert it into the body, and a method of deforming it upon insertion.

The insertion device of the invention may be of any type, as long as it includes at least a tubular holder capable of holding the inter-organ spacer of the invention therein. Examples of the insertion device include an introducer-type insertion device including the tubular holder and ejecting means for ejecting the inter-organ spacer held in the tubular holder, a first extractor-type insertion device including the tubular holder and pulling means for pulling the inter-organ spacer into the tubular holder, and a second extractor-type insertion device including the tubular holder and a funnel portion provided at one end of the tubular holder.

The tubular holder may be in any shape, as long as the inter-organ spacer of the invention can be held therein in a compressed, wound or folded state or as it is. For example, the tubular holder may be in the shape of a cylinder with a circular or elliptic cross-section, a tube with a polygonal cross-section, or the like. The tubular holder may be of any size, as long as the whole or part thereof can be inserted into a trocar. For example, when the tubular holder is in the shape of a circular cylinder, the tubular holder may have an outer diameter smaller than the inner diameter of a trocar so that it can be inserted into the trocar.

Figure 6:
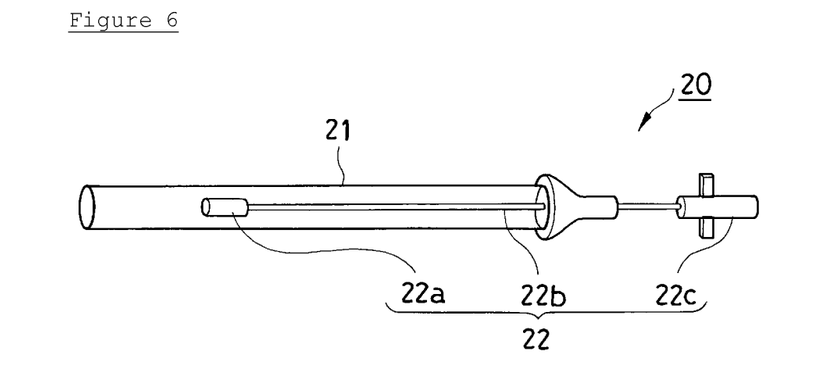
FIG. 6 is a perspective view schematically showing an aspect of an insertion device of the invention.

FIG. 6 shows an example of the introducer-type insertion device including a tubular holder and ejecting means. An introducer-type insertion device 20 shown in FIG. 6 includes a tubular holder 21 capable of holding the inter-organ spacer (not shown) therein and ejecting means 22 capable of ejecting the inter-organ spacer held in the tubular holder. The ejecting means includes a pressing pad 22a for directly contacting with the inter-organ spacer, a pressing rod 22b joined to the pressing pad, and an operating grip 22c joined to the other end of the pressing rod. In the invention, the inter-organ spacer may be provided in such a form that it has previously been inserted in the introducer-type insertion device, or the inter-organ spacer and the introducer-type insertion device may be provided separately, and the inter-organ spacer may be placed in the insertion device at the time of endoscopic surgery.

Figure 7:
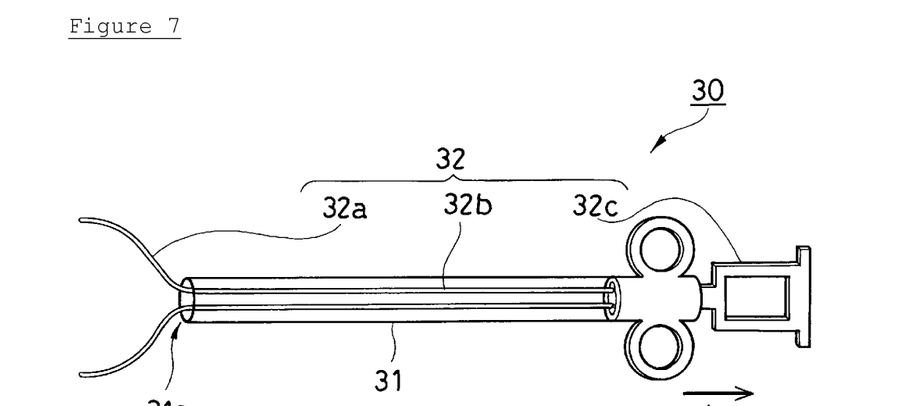
FIG. 7 is a perspective view schematically showing another aspect of the insertion device of the invention.

FIG. 7 shows an example of the first extractor-type insertion device including a tubular holder and pulling means. An extractor-type insertion device 30 shown in FIG. 7 includes a tubular holder 31 capable of holding the inter-organ spacer (not shown) therein and pulling means 32 capable of pulling the inter-organ spacer into the tubular holder. The pulling means 32 includes a grasping portion 32a capable of grasping the inter-organ spacer, a handle 32c for manipulating the grasping portion, and a joint 32b that joins the grasping portion and the handle. When the handle 32c is pulled (namely, shifted in the direction indicated by arrow A in FIG. 7), the joint 32b is also shifted in the direction of arrow A, so that the ends of the grasping portion 32a are closed to make it possible to grasp the inter-organ spacer. When the handle 32c is further pulled, the inter-organ spacer grasped by the grasping portion 32a can be pulled into the tubular holder 31. The inter-organ spacer held in the tubular holder 31 may be ejected from the tubular holder 31 by detaching the pulling means 32 from the insertion device 30 and using suitable ejecting means (not shown) in place of it.

Figure 8:
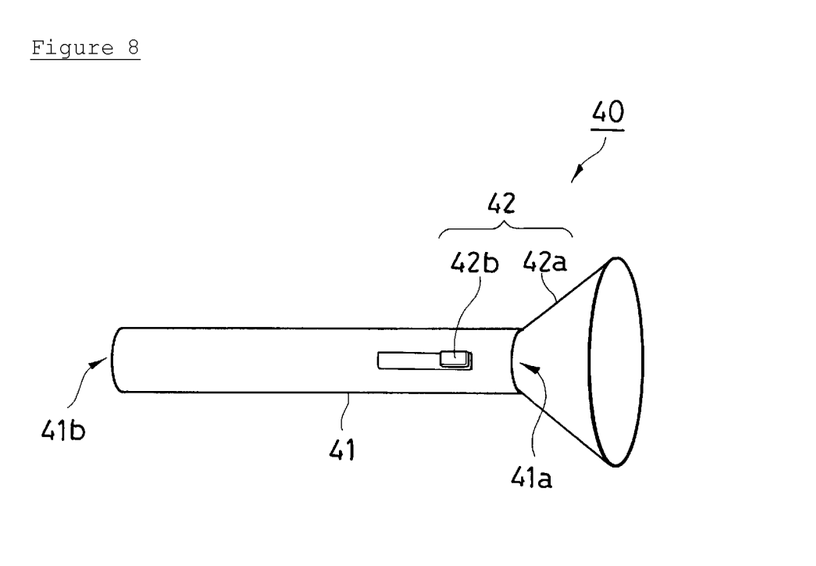
FIG. 8 is a perspective view schematically showing still another aspect of the insertion device of the invention.
Figure 9:
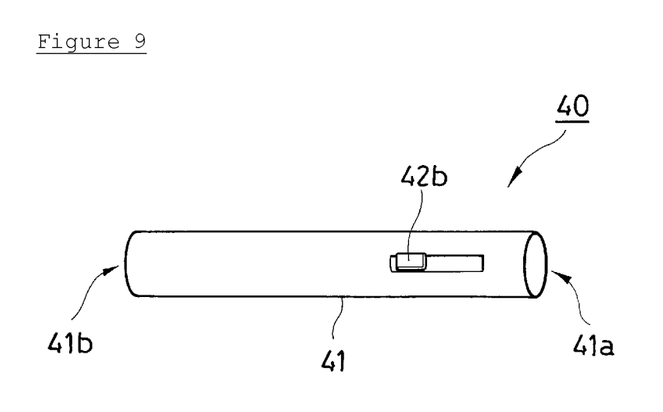
FIG. 9 is a perspective view schematically showing a state in which a main funnel body of the insertion device shown in FIG. 8 is housed.

FIGS. 8 and 9 show an example of the second extractor-type insertion device including a tubular holder and a funnel portion. An extractor-type insertion device 40 shown in FIGS. 8 and 9 includes a tubular holder 41 capable of holding the inter-organ spacer (not shown) therein and a funnel portion 42 provided at one end 41a of the tubular holder. A main funnel body 42a of the funnel portion 42 shown in FIG. 8 can be housed in the tubular holder 41 by manipulating a slidable knob 42b as shown in FIG. 9. When the inter-organ spacer is placed into the tubular holder, the main funnel body 42a may be opened as shown in FIG. 8 so that the inter-organ spacer can be placed into the tubular holder from the end 41a. On the other hand, when the inter-organ spacer is ejected from the tubular holder, the main funnel body 42a may be housed in the tubular holder 41 as shown in FIG. 9, and in this state, suitable ejecting means may be inserted from one of the ends 41a and 41b into the tubular holder 41 so that the inter-organ spacer can be ejected from the other end to the outside of the tubular holder.

The extractor-type insertion device of the invention (including the first and second extractor-type insertion devices) may be used not only to insert the inter-organ spacer into the body but also to take the inter-organ spacer out of the body by a similar process after surgery, which makes it possible to place the inter-organ spacer in the tubular holder. Therefore, the extractor-type insertion device of the invention may be used for both purposes, i.e., insertion into the body and removal to the outside of the body.

In the case of the extractor-type insertion device shown in FIG. 7, for example, an end portion 31a having the grasping portion 32a may be inserted into the body through an incision in the body surface (for example, through a trocar), and the pulling means 32 may be operated so that the inter-organ spacer can be recovered from the body into the tubular holder 31. Alternatively, in the case of the extractor-type insertion device shown in FIGS. 8 and 9, the end portion 41a may be inserted into the body through an incision in the body surface, and the main funnel body 42a may be opened so that the inter-organ spacer can be recovered from the body into the tubular holder 41. In this case, the pulling means 32 shown in FIG. 7 may be inserted from the end portion 41b of the tubular holder 41 so that the inter-organ spacer can be more easily recovered into the tubular holder 41.

The endoscopic surgery kit of the invention may be of any type, as long as it includes the inter-organ spacer of the invention and the insertion device of the invention. The endoscopic surgery kit of the invention may be provided in such a form that the inter-organ spacer is originally placed in the insertion device. Alternatively, the inter-organ spacer and the insertion device may be provided separately, and the inter-organ spacer may be placed in the insertion device at the time of endoscopic surgery. The inter-organ spacer is preferably provided in such a form that it is placed in the insertion device, so that it can be sterilized.

EXAMPLES

The present invention will now be further illustrated by, but is by no means limited to, the following Examples.

Example 1

Evaluation of Liquid Absorbency

This example and each example described below were performed using three porous soft materials (hereinafter referred to as sample set A): a polyurethane material with low liquid releasing ability (Toughponge (Hogy Medical Co., Ltd.)); a polyurethane material with high liquid releasing ability for abdominal surgery; and a polyvinyl alcohol material (Retractor Pad (Heiwa Iryo Kikai Co., Ltd.)). Another sample set used includes six materials (hereinafter referred to as sample set B): the polyurethane material with low liquid release ability (Toughponge (Hogy Medical Co., Ltd.), hereinafter also referred to as sample A); four different polyurethane materials with high liquid releasing ability (hereinafter also referred to as samples B to E); and a polyethylene material (hereinafter also referred to as sample F). Table 2 shows the principal properties of each porous soft material used in sample sets A and B. The elongation in Table 2 was measured according to JIS K 6400-5 (2004).

TABLE 2

| Samples | Material | Density (kg/m³) | Number of cells (cells/25 mm) | Elongation (%) |
|---|---|---|---|---|
| A | PU (L) | 75 ± 10 | ≥60 | 300~400 |
| B | PU (H) | 30 ± 3 | ≥50 | 250~350 |
| C | PU (H) | 16 ± 2 | 25 ± 10 | 70~120 |
| D | PU (H) | 22 ± 3 | (—) | 50~130 |
| E | PU (H) | 31 ± 2 | 50 ± 5 | 250~350 |
| F | PE | 44 | (—) | 100~200 |
| b | PU (H) | 16 ± 1.5 | 30 ± 10 | 100~200 |

PU (L): Polyurethane with low liquid releasing ability
PU (H): Polyurethane with high liquid releasing ability
PE: Polyethylene (1) Evaluation of Liquid Absorbency of Sample Set A The weight (Wd in units of g) of the sample (in the shape of a rectangular parallelepiped of 20 mm×20 mm×10 mm) was measured before it was immersed in artificial blood. The sample was then gently dropped into a 100 mL-volume beaker containing 50 mL of artificial blood (Synthetic Blood Reagent Mix (Johnson, Moen & Co.)) and allowed to stand for 3 minutes. Thereafter, the sample was gently taken out using tweezers and placed on a wire mesh for 30 seconds so that the artificial blood was allowed to drip. The sample was then placed in another beaker, and the weight (Ww in units of g) of the sample was measured. The liquid absorbency was calculated from the following formula: $(Ww-Wd) \div Wd \times 100$ (%).

The results are shown in Table 3. Three samples were prepared for each material, and the average of the absorbencies (%) of the respective samples was calculated. The higher value indicates the higher liquid absorbency.

TABLE 3

| Porous soft materials | Wd | Ww | Liquid absorbency | Average |
|---|---|---|---|---|
| PU (L) | 0.73 | 3.02 | 313.7 | 390.8 |
|  | 0.62 | 2.82 | 354.8 |  |
|  | 0.51 | 3.08 | 503.9 |  |
| PU (H) | 0.26 | 0.48 | 84.6 | 88.5 |
|  | 0.26 | 0.66 | 153.8 |  |
|  | 0.37 | 0.47 | 27.0 |  |
| PVA | 1.88 | 4.11 | 118.6 | 138.7 |
|  | 1.71 | 3.53 | 106.4 |  |
|  | 1.43 | 4.16 | 190.9 |  |

PU (L): Polyurethane with low liquid releasing ability
PU (H): Polyurethane with high liquid releasing ability
PVA: Polyvinyl alcohol (2) Evaluation of Liquid Absorbency of Sample Set B The sample (in the shape of a rectangular parallelepiped of 50 mm×50 mm×20 mm) was allowed to absorb a sufficient amount of artificial blood, and then it was sufficiently wrung. The lid of a disposable Petri dish with a diameter of 9 cm was turned upside down and placed on a table, and 20 mL of artificial blood was placed therein. The sample wrung sufficiently was placed therein, and the sample was pressed five times with the bottom surface of the Petri dish. In this process, the sample was pressed until it was no longer compressible, and the pressing was performed about once per second. The sample was taken out, and the amount (V in units of mL) of the artificial blood left in the lid of the Petri dish was measured. The liquid absorbency was calculated from the following formula: $(20 \text{ mL}-V)/20 \text{ mL} \times 100$(%).

The results are shown in Table 4. Three samples were prepared for each material, and the average of the absorbencies (%) of the respective samples was calculated. The higher value indicates the higher liquid absorbency.

TABLE 4

| Porous soft materials | Sample No. | Amount of liquid left in lid of Petri dish | Liquid absorbency (%) | Average |
|---|---|---|---|---|
| A | 1 | 3.5 | 82.5 | 82.3 |
|  | 2 | 3.6 | 82.0 |  |
|  | 3 | 3.5 | 82.5 |  |
| B | 1 | 2.0 | 90.0 | 90.7 |
|  | 2 | 1.4 | 93.0 |  |
|  | 3 | 2.2 | 89.0 |  |
| C | 1 | 2.2 | 89.0 | 89.3 |
|  | 2 | 2.0 | 90.0 |  |
|  | 3 | 2.2 | 89.0 |  |
| D | 1 | 2.3 | 88.5 | 85.8 |
|  | 2 | 3.4 | 83.0 |  |
|  | 3 | 2.8 | 86.0 |  |
| E | 1 | 2.0 | 90.0 | 90.2 |
|  | 2 | 1.8 | 91.0 |  |
|  | 3 | 2.1 | 89.5 |  |
| F | 1 | 11.6 | 42.0 | 44.5 |
|  | 2 | 11.2 | 44.0 |  |
|  | 3 | 10.5 | 47.5 |  |

Example 2

Evaluation of Liquid Holding Ability

The weight (Wd in units of g) of the sample (in the shape of a rectangular parallelepiped of 20 mm×20 mm×80 mm) was measured before it was allowed to absorb artificial blood. After the sample was allowed to absorb a sufficient amount of artificial blood (Synthetic Blood Reagent Mix (Johnson, Moen & Co.)), its weight (Ww in units of g) was measured. Subsequently, the sample was placed on a polyvinyl chloride plate, and the plate was allowed to stand for 3 minutes, while being tilted at 45°. Thereafter, the weight ($W_3$ in units of g) of the sample was measured.

The liquid holding ability was calculated from the following formula: $(W_3-Wd) \div (Ww-Wd) \times 100$(%).

The results on sample sets A and B are shown in Tables 5 and 6, respectively. Three samples were prepared for each material, and the average of the liquid holding abilities (%) of the respective samples was calculated. The higher value indicates the higher liquid holding ability.

TABLE 5

| Porous soft materials | Wd | Ww | W3 | Liquid holding ability | Average |
|---|---|---|---|---|---|
| PU (L) | 2.34 | 25.13 | 24.62 | 97.8 | 97.0 |
|  | 2.74 | 21.97 | 21.40 | 97.0 |  |
|  | 2.69 | 22.81 | 22.05 | 96.2 |  |
| PU (H) | 0.63 | 15.10 | 14.62 | 96.7 | 96.7 |
|  | 0.53 | 20.54 | 19.38 | 94.2 |  |
|  | 0.58 | 16.88 | 16.75 | 99.2 |  |
| PVA | 13.22 | 20.15 | 19.84 | 95.5 | 93.5 |
|  | 13.18 | 17.20 | 16.90 | 92.5 |  |
|  | 13.20 | 17.77 | 17.42 | 92.3 |  |

PU (L): Polyurethane with low liquid releasing ability
PU (H): Polyurethane with high liquid releasing ability
PVA: Polyvinyl alcohol

TABLE 6

| Porous soft materials | Sample No. | Wd | Ww | W3 | Liquid holding ability | Average |
|---|---|---|---|---|---|---|
| A | 1 | 3.6 | 37.9 | 36.8 | 96.7 | 98.3 |
|   | 2 | 3.9 | 36.5 | 36.1 | 98.8 |   |
|   | 3 | 3.9 | 37.4 | 37.3 | 99.4 |   |
| B | 1 | 1.5 | 36.3 | 36.3 | 100.0 | 100.0 |
|   | 2 | 1.5 | 38.5 | 38.5 | 100.0 |   |
|   | 3 | 1.5 | 39.4 | 39.4 | 100.0 |   |
| C | 1 | 0.8 | 43.1 | 40.4 | 93.6 | 92.3 |
|   | 2 | 0.8 | 44.0 | 40.6 | 92.1 |   |
|   | 3 | 0.8 | 42.8 | 39.1 | 91.2 |   |
| D | 1 | 1.1 | 38.7 | 37.7 | 97.3 | 97.6 |
|   | 2 | 1.1 | 38.7 | 37.4 | 96.5 |   |
|   | 3 | 1.1 | 36.6 | 36.2 | 98.9 |   |
| E | 1 | 1.5 | 44.1 | 44.1 | 100.0 | 100.0 |
|   | 2 | 1.5 | 43.6 | 43.6 | 100.0 |   |
|   | 3 | 1.5 | 44.6 | 44.6 | 100.0 |   |
| F | 1 | 2.6 | 39.0 | 38.0 | 97.3 | 96.5 |
|   | 2 | 2.5 | 40.0 | 38.5 | 96.0 |   |
|   | 3 | 2.5 | 38.7 | 37.3 | 96.1 |   |

Example 3

Evaluation of Liquid Releasing Ability

The weight (Wd in units of g) of the sample (in the shape of a rectangular parallelepiped of 20 mm×50 mm×50 mm) was measured before it was allowed to absorb artificial blood. After the sample was allowed to absorb a sufficient amount of artificial blood (Synthetic Blood Reagent Mix (Johnson, Moen & Co.)), it was placed on a plastic plate, and its weight (Ww in units of g) was measured. The artificial blood was sucked under a reduced pressure of −600 to −650 mmHg (−80 to −85 kPa) for 1 minute, while the tip of a Yanker suction tube was held to the center of the sample and pushed in. After the suction, the weight (Ws in units of g) of the sample being placed on the plastic plate was measured. The liquid releasing ability was calculated from the following formula: (Ww−Ws)÷(Ww−Wd)×100(%).

The results on sample sets A and B are shown in Tables 7 and 8, respectively. Three samples were prepared for each material, and the average of the liquid releasing abilities (%) of the respective samples was calculated. The higher value indicates the higher liquid releasing ability.

TABLE 7

| Porous soft materials | Wd | Ww | Ws | Liquid releasing ability | Average |
|---|---|---|---|---|---|
| PU (L) | 7.97 | 39.56 | 33.34 | 19.7 | 21.6 |
|   | 7.38 | 49.87 | 41.47 | 19.8 |   |
|   | 7.61 | 45.48 | 35.83 | 25.5 |   |
| PU (H) | 2.61 | 39.68 | 18.95 | 55.9 | 62.8 |
|   | 1.99 | 35.74 | 13.38 | 66.3 |   |
|   | 2.65 | 33.64 | 13.13 | 66.2 |   |
| PVA | 19.42 | 45.16 | 36.70 | 32.9 | 24.8 |
|   | 19.20 | 42.52 | 35.52 | 30.0 |   |
|   | 20.37 | 46.10 | 43.11 | 11.6 |   |

PU (L): Polyurethane with low liquid releasing ability
PU (H): Polyurethane with high liquid releasing ability
PVA: Polyvinyl alcohol

TABLE 8

| Porous soft materials | Sample No. | Wd | Ww | Ws | Liquid releasing ability (%) | Average |
|---|---|---|---|---|---|---|
| A | 1 | 3.6 | 37.7 | 30.2 | 22.0 | 19.5 |
|   | 2 | 3.9 | 36.3 | 30.7 | 17.2 |   |
|   | 3 | 3.9 | 37.3 | 30.8 | 19.3 |   |
| B | 1 | 1.5 | 38.0 | 14.5 | 64.4 | 67.5 |
|   | 2 | 1.5 | 38.4 | 13.0 | 68.8 |   |
|   | 3 | 1.5 | 40.2 | 13.4 | 69.3 |   |
| C | 1 | 0.8 | 42.4 | 5.5 | 88.6 | 87.8 |
|   | 2 | 0.8 | 40.9 | 5.0 | 89.4 |   |
|   | 3 | 0.8 | 40.7 | 6.6 | 85.4 |   |
| D | 1 | 1.1 | 39.2 | 7.7 | 82.7 | 80.1 |
|   | 2 | 1.1 | 38.8 | 8.5 | 80.4 |   |
|   | 3 | 1.1 | 35.0 | 8.8 | 77.3 |   |
| E | 1 | 1.5 | 44.0 | 9.1 | 82.1 | 85.2 |
|   | 2 | 1.5 | 45.2 | 7.1 | 87.2 |   |
|   | 3 | 1.5 | 46.4 | 7.7 | 86.2 |   |
| F | 1 | 2.6 | 39.9 | 35.0 | 13.1 | 12.8 |
|   | 2 | 2.5 | 38.5 | 33.9 | 12.8 |   |
|   | 3 | 2.5 | 38.6 | 34.1 | 12.5 |   |

Example 4

Evaluation of Compressive Residual Strain

The thickness ($t_0$) of the center of the test piece (50 mm×50 mm×20 mm) was measured in increments of 0.1 mm with a vernier caliper, while its form was not changed. Subsequently, the thickness of the test piece was reduced to 50% using two compression plates. Within at most 15 minutes, the test piece being compressed was placed in a thermostatic chamber at a temperature of 70±1° C. and heated for 22 hours. The test piece was taken out of the thermostatic chamber, separated from the compression plates within 1 minute, and placed on a polyvinyl chloride plate. The test piece was allowed to stand at a temperature of 23±2° C. and a relative humidity of 50±5% (in a chamber controlled for 16 hours or more) for 30 minutes to be restored, and then the thickness ($t_1$) of the same portion was measured in increments of 0.1 mm. The compressive residual strain (%) was calculated from the following formula: $(t_0-t_1) \div t_0 \times 100(\%)$.

The results on sample sets A and B are shown in Tables 9 and 10, respectively. Three samples were prepared for each material, and the average of the compressive residual strains (%) of the respective samples was calculated. When the polyvinyl alcohol material was treated at 70° C., the water was removed, so that it became dried and lost the flexibility. The higher compressive residual strain value indicates the higher ability to retain shape.

TABLE 9

| Porous soft materials | $t_o$ | $t_1$ | Compressive residual strain | Average |
|---|---|---|---|---|
| PU (L) | 19.8 | 18.9 | 4.5 | 4.9 |
|   | 19.8 | 18.8 | 5.1 |   |
|   | 19.7 | 18.7 | 5.1 |   |
| PU (H) | 20.0 | 18.5 | 7.5 | 3.3 |
|   | 20.1 | 20.0 | 0.5 |   |
|   | 20.3 | 19.9 | 2.0 |   |
| PVA | 20.1 | 10.9 | 45.8 | 46.6 |
|   | 20.3 | 10.3 | 49.3 |   |
|   | 19.9 | 11.0 | 44.7 |   |

PU (L): Polyurethane with low liquid releasing ability
PU (H): Polyurethane with high liquid releasing ability
PVA: Polyvinyl alcohol

TABLE 10

| Porous soft materials | Sample No. | $t_o$ | $t_1$ | Compressive residual strain (%) | Average |
|---|---|---|---|---|---|
| A | 1 | 20.1 | 19.6 | 2.5 | 2.5 |
|  | 2 | 20.1 | 19.6 | 2.5 |  |
|  | 3 | 20.1 | 19.6 | 2.5 |  |
| B | 1 | 20.5 | 19.9 | 2.9 | 2.9 |
|  | 2 | 20.4 | 19.8 | 2.9 |  |
|  | 3 | 20.4 | 19.8 | 2.9 |  |
| C | 1 | 20.1 | 19.2 | 4.5 | 4.6 |
|  | 2 | 20.1 | 19.2 | 4.5 |  |
|  | 3 | 20.1 | 19.1 | 5.0 |  |
| D | 1 | 20.1 | 18.9 | 6.0 | 4.5 |
|  | 2 | 20.0 | 19.3 | 3.5 |  |
|  | 3 | 19.9 | 19.1 | 4.0 |  |
| E | 1 | 20.2 | 19.9 | 1.5 | 1.3 |
|  | 2 | 20.1 | 19.9 | 1.0 |  |
|  | 3 | 20.1 | 19.8 | 1.5 |  |
| F | 1 | 21.2 | 10.8 | 49.1 | 48.3 |
|  | 2 | 21.2 | 11.3 | 46.7 |  |
|  | 3 | 21.2 | 10.8 | 49.1 |  |

Example 5

Evaluation of Hardness (Flexibility)

A laminate of two sample pieces of 80×80×20 mm was used as the test object. The test object (40 mm in thickness) was placed on the mount of a tester, and a pressing plate (33.7 mm in diameter) was placed on the upper surface of the sample piece so that a load of 0.2 N was applied. The pressing plate was then pushed in 10 mm at a rate of 100±20 mm/minute, and immediately thereafter, the load was removed. Once again, the pressing plate was pushed in 30 mm at a rate of 100±20 mm/minute, and 20 seconds after the stop, the load (N) was recorded. The results on sample sets A and B are shown in Tables 11 and 12, respectively. Three samples were prepared for each material, and the average of the hardnesses (N) of the respective samples was calculated.

TABLE 11

| Porous soft materials | Hardnesses (N) | Average |
|---|---|---|
| PU (L) | 31.3 | 32.8 |
|  | 34.3 |  |
|  | 32.8 |  |
| PU (H) | 18.0 | 17.3 |
|  | 16.8 |  |
|  | 17.2 |  |
| PVA | 208.0 | 214.3 |
|  | 212.0 |  |
|  | 223.0 |  |

PU (L): Polyurethane with low liquid releasing ability
PU (H): Polyurethane with high liquid releasing ability
PVA: Polyvinyl alcohol

TABLE 12

| Porous soft materials | Sample No. | Hardnesses (N) | Average |
|---|---|---|---|
| A | 1 | 42.3 | 40.4 |
|  | 2 | 39.3 |  |
|  | 3 | 39.7 |  |
| B | 1 | 20.7 | 21.3 |
|  | 2 | 21.2 |  |
|  | 3 | 22.0 |  |

TABLE 12-continued

| Porous soft materials | Sample No. | Hardnesses (N) | Average |
|---|---|---|---|
| C | 1 | 13.4 | 13.6 |
|  | 2 | 13.3 |  |
|  | 3 | 14.1 |  |
| D | 1 | 22.5 | 21.4 |
|  | 2 | 20.5 |  |
|  | 3 | 21.2 |  |
| E | 1 | 26.5 | 26.6 |
|  | 2 | 27.3 |  |
|  | 3 | 26.1 |  |
| F | 1 | 65.9 | 64.5 |
|  | 2 | 63.5 |  |
|  | 3 | 64.1 |  |

Example 6

Evaluation of Impact Resilience

A laminate of two sample pieces of 80×80×20 mm was used as the test object. A ⅝ chrome steel ball specified in JIS B 1501 was placed 476 mm above the test object and allowed to freely fall. The uppermost level of the bounding steel ball was measured. In the quantification, the positions 16 mm and 476 mm above the sample piece were normalized as 0 and 100, respectively. The results on sample sets A and B are shown in Tables 13 and 14, respectively. Three samples were prepared for each material, and the average of the impact resiliences of the respective samples was calculated.

TABLE 13

| Porous soft materials | Measured value (mm) | Impact resilience | Average |
|---|---|---|---|
| PU (L) | 155 | 33.7 | 34.1 |
|  | 155 | 33.7 |  |
|  | 160 | 34.8 |  |
| PU (H) | 180 | 39.1 | 38.8 |
|  | 180 | 39.1 |  |
|  | 175 | 38.0 |  |
| PVA | 35 | 7.6 | 8.0 |
|  | 40 | 8.7 |  |
|  | 35 | 7.6 |  |

PU (L): Polyurethane with low liquid releasing ability
PU (H): Polyurethane with high liquid releasing ability
PVA: Polyvinyl alcohol

TABLE 14

| Porous soft materials | Sample No. | Measured value (mm) | Impact resilience | Average |
|---|---|---|---|---|
| A | 1 | 23.0 | 50.0 | 48.9 |
|  | 2 | 22.0 | 47.8 |  |
|  | 3 | 22.5 | 48.9 |  |
| B | 1 | 20.5 | 44.6 | 44.6 |
|  | 2 | 20.5 | 44.6 |  |
|  | 3 | 20.5 | 44.6 |  |
| C | 1 | 26.5 | 57.6 | 57.6 |
|  | 2 | 26.0 | 56.5 |  |
|  | 3 | 27.0 | 58.7 |  |
| D | 1 | 25.5 | 55.4 | 54.7 |
|  | 2 | 25.0 | 54.3 |  |
|  | 3 | 25.0 | 54.3 |  |
| E | 1 | 20.5 | 44.6 | 43.8 |
|  | 2 | 20.0 | 43.5 |  |
|  | 3 | 20.0 | 43.5 |  |
| F | 1 | 17.0 | 37.0 | 36.6 |
|  | 2 | 16.0 | 34.8 |  |
|  | 3 | 17.5 | 38.0 |  |

Example 7

Evaluation of Tensile Strength

According to JIS K 6400-5 (2004), a 1 cm-thick No. 2 test piece was prepared. While the test piece was pulled at a rate of 500 mm/minute, the maximum load was measured until the test piece was ruptured. The results on sample sets A and B are shown in Tables 15 and 16, respectively. Three samples (sample set A) or five samples (sample set B) were prepared for each material, and the average of the tensile strengths (N) of the respective samples was calculated.

TABLE 15

| Porous soft materials | Tensile strength (N) | Average |
|---|---|---|
| PU (L) | 37.2 | 33.7 |
|  | 36.9 |  |
|  | 27.0 |  |
| PU (H) | 7.4 | 7.6 |
|  | 8.1 |  |
|  | 7.3 |  |
| PVA | 40.6 | 46.3 |
|  | 47.9 |  |
|  | 50.5 |  |

PU (L): Polyurethane with low liquid releasing ability
PU (H): Polyurethane with high liquid releasing ability
PVA: Polyvinyl alcohol

TABLE 16

| Porous soft materials | Sample No. | Tensile strength (N) | Average |
|---|---|---|---|
| A | 1 | 36.4 | 35.5 |
|  | 2 | 35.3 |  |
|  | 3 | 35.2 |  |
|  | 4 | 35.9 |  |
|  | 5 | 34.4 |  |
| B | 1 | 23.3 | 23.2 |
|  | 2 | 23.2 |  |
|  | 3 | 22.9 |  |
|  | 4 | 22.8 |  |
|  | 5 | 23.7 |  |
| C | 1 | 8.9 | 9.0 |
|  | 2 | 8.7 |  |
|  | 3 | 9.1 |  |
|  | 4 | 9.1 |  |
|  | 5 | 9.3 |  |
| D | 1 | 9.2 | 9.0 |
|  | 2 | 8.6 |  |
|  | 3 | 9.3 |  |
|  | 4 | 8.0 |  |
|  | 5 | 9.9 |  |
| E | 1 | 26.2 | 25.3 |
|  | 2 | 23.2 |  |
|  | 3 | 25.1 |  |
|  | 4 | 26.1 |  |
|  | 5 | 26.0 |  |
| F | 1 | 22.5 | 22.9 |
|  | 2 | 22.3 |  |
|  | 3 | 23.1 |  |
|  | 4 | 23.1 |  |
|  | 5 | 23.7 |  |

Example 8

Evaluation of Degree of Swelling

Fifty mL of artificial blood (Synthetic Blood Reagent Mix (Johnson, Moen & Co.)) was put in a 100 mL volume beaker. The sample whose dimensions (length, width and height) had been previously measured (about 20 mm×20 mm×10 mm) was gently dropped into the artificial blood-containing beaker and allowed to stand for 3 minutes. Thereafter, the sample was gently taken out with tweezers and placed on a wire mesh for 30 seconds so that the artificial blood was allowed to drip. Thereafter, the dimensions of the sample were measured again. The degree of swelling was calculated from the following formula: $(V_w/V_d) \times 100(\%)$, wherein $V_w$ is the volume of the sample after the liquid absorption, and $V_d$ is the volume of the sample before the liquid absorption. The results on sample set B are shown in Table 17. Three samples were prepared for each material, and the average of the degrees (%) of swelling of the respective samples was calculated.

TABLE 17

| Porous soft materials | Sample No. | Before liquid absorption | | | | After liquid absorption | | | | Degree of swelling | |
|---|---|---|---|---|---|---|---|---|---|---|---|
| | | Length | Width | Height | Volume | Length | Width | Height | Volume | | Average |
| A | 1 | 51.1 | 50.3 | 20.4 | 52434.7 | 51.2 | 50.8 | 20.3 | 52799.5 | 100.7 | 104.4 |
|  | 2 | 50.8 | 50.7 | 20.1 | 51768.8 | 50.7 | 50.5 | 21 | 53767.4 | 103.9 |  |
|  | 3 | 50 | 50 | 20.3 | 50750.0 | 52 | 51.7 | 20.5 | 55112.2 | 108.6 |  |
| B | 1 | 49.7 | 50.9 | 20.7 | 52365.4 | 50.3 | 51.0 | 20.6 | 52845.2 | 100.9 | 100.2 |
|  | 2 | 50.3 | 50.1 | 20.3 | 51156.6 | 50.5 | 50.3 | 20.2 | 51311.0 | 100.3 |  |
|  | 3 | 49.4 | 50.6 | 20.6 | 51492.6 | 49.6 | 50.6 | 20.4 | 51199.1 | 99.4 |  |
| C | 1 | 50.4 | 50.0 | 20.0 | 50400.0 | 49.7 | 50.4 | 20.2 | 50598.6 | 100.4 | 100.8 |
|  | 2 | 50.4 | 50.0 | 20.2 | 50904.0 | 50.4 | 50.4 | 20.1 | 51057.2 | 100.3 |  |
|  | 3 | 50.2 | 50.4 | 20.0 | 50601.6 | 50.4 | 50.6 | 20.2 | 51514.8 | 101.8 |  |
| D | 1 | 50.4 | 49.9 | 19.7 | 49544.7 | 50.5 | 49.9 | 19.9 | 50147.0 | 101.2 | 100.4 |
|  | 2 | 50.4 | 50.0 | 20.0 | 50400.0 | 50.1 | 50.0 | 20.1 | 50350.5 | 99.9 |  |
|  | 3 | 49.8 | 49.8 | 20.1 | 49848.8 | 49.9 | 50.0 | 20.0 | 49900.0 | 100.1 |  |
| E | 1 | 50.2 | 50.4 | 20.2 | 51107.6 | 50.4 | 49.9 | 20.1 | 50550.7 | 98.9 | 99.8 |
|  | 2 | 50.1 | 50.4 | 20.1 | 50753.3 | 50.3 | 50.1 | 20.2 | 50904.6 | 100.3 |  |
|  | 3 | 50.0 | 50.0 | 20.1 | 50250.0 | 50.1 | 50.3 | 20.0 | 50400.6 | 100.3 |  |
| F | 1 | 52.1 | 51.2 | 21.2 | 56551.4 | 51.9 | 52.4 | 21.1 | 57382.7 | 101.5 | 103.2 |
|  | 2 | 50.4 | 50.4 | 20.1 | 51057.2 | 50.5 | 51.0 | 20.5 | 52797.8 | 103.4 |  |
|  | 3 | 50.8 | 50.6 | 20.1 | 51666.6 | 50.9 | 50.2 | 21.2 | 54169.8 | 104.8 |  |

Example 9

Evaluation of the Ability to Indirectly Absorb Liquid

The sample (in the shape of a rectangular parallelepiped of 80 mm×80 mm×20 mm) was allowed to stand in a vessel of 12 cm×23 cm×5 cm containing 50 mL of artificial blood, and the upper surface of the sample was repeatedly pushed, so that a sufficient amount of artificial blood was absorbed in the sample. After it was confirmed that a sufficient amount of artificial blood not absorbed was left around the sample, the top of a suction tip was held to the center of the sample. The artificial blood was sucked under a reduced pressure of −600 to −650 mmHg (−80 to −85 kPa), while the suction tip was pushed in. It was checked whether or not the whole amount of the artificial blood in and around the sample was removed after the suction for a sufficient period of time. The results are shown in Table 18. The suction time was set to 1 minute. In the table, the mark "-" means that even after the suction for 1 minute, the artificial blood left around the sample was not removed.

TABLE 18

| Porous soft materials | Results |
| --- | --- |
| A | — |
| B | ◯ |
| C | ◯ |
| D | ◯ |
| E | — |
| F | — |

Example 10

Preparation of Inter-Organ Spacers

The polyurethane materials with low liquid releasing ability and with high liquid releasing ability, which were used for the evaluations in Examples 1 to 9, were each cut into pieces with the shapes and the sizes shown below to form inter-organ spacers according to the invention.

(A) Rectangular Solids (Length×Width×Thickness)
(1) 50 mm×50 mm×5 mm
(2) 50 mm×50 mm×10 mm
(3) 50 mm×50 mm×20 mm
(4) 50 mm×50 mm×30 mm
(5) 50 mm×50 mm×50 mm
(6) 80 mm×80 mm×5 mm
(7) 80 mm×80 mm×10 mm
(8) 80 mm×80 mm×20 mm
(9) 80 mm×80 mm×30 mm
(10) 80 mm×80 mm×50 mm
(11) 100 mm×100 mm×5 mm
(12) 100 mm×100 mm×10 mm
(13) 100 mm×100 mm×20 mm
(14) 100 mm×100 mm×30 mm
(15) 100 mm×100 mm×50 mm
(B) Cubes (Side Length)
(1) 20 mm
(2) 30 mm
(3) 40 mm
(4) 50 mm
(5) 80 mm
(6) 100 mm
(C) Discs (Diameter×Thickness)
(1) 50 mm diameter×5 mm thickness
(2) 50 mm diameter×10 mm thickness
(3) 50 mm diameter×20 mm thickness
(4) 50 mm diameter×30 mm thickness
(5) 50 mm diameter×50 mm thickness
(6) 80 mm diameter×5 mm thickness
(7) 80 mm diameter×10 mm thickness
(8) 80 mm diameter×20 mm thickness
(9) 80 mm diameter×30 mm thickness
(10) 80 mm diameter×100 mm thickness
(11) 100 mm diameter×5 mm thickness
(12) 100 mm diameter×10 mm thickness
(13) 100 mm diameter×20 mm thickness
(14) 100 mm diameter×30 mm thickness
(15) 100 mm diameter×50 mm thickness Among these inter-organ spacers, the low-liquid-releasing-ability polyurethane spacer in the shape of a rectangular solid (A)-(1), (2), (6), or (7), a cube (B)-(1), or a disc (C)-(1), (2), (6), or (7) was able to be inserted into a tubular holder with an inner diameter of 11 mm by deforming the spacer by hand and pushing it into the holder from one end thereof. It was also demonstrated that the high-liquid-releasing-ability polyurethane spacer in the shape of a rectangular solid (A)-(1), (2), or (3), or a disc (C)-(1), (2), or (3) was able to be inserted into a tubular holder with an inner diameter of 11 mm by deforming the spacer by hand and pushing it into the holder from one end thereof. The spacer in the shape of a rectangular solid (A)-(3), (4), (11), or (12), a cube (B)-(2), or a disc (C)-(3), (4), (11), or (12) was also able to be inserted into a tubular holder with an inner diameter of 15 mm in the same manner.

Industrial Applicability

The inter-organ spacer of the invention is suitable for use in endoscopic surgery applications. As above, the present invention was explained with reference to particular embodiments, and modifications and improvements obvious to those skilled in the art are included in the scope of the present invention.

The invention claimed is:

1. An inter-organ spacer for use in endoscopic surgery, consisting of a sponge formed of a porous soft material having an ability to temporarily store liquid and an ability to retain its shape, and an X-ray contrast agent contained in the sponge, and wherein the porous soft material has a liquid absorbency ranging from 40% to 100%, a liquid holding ability ranging from 90% to 100%, and a liquid releasing ability ranging from 40% to 100%, wherein the porous soft material is selected from the group consisting of polyurethane, polyvinyl alcohol, cellulose, and polyethylene, wherein a tensile strength of the porous soft material is 15 to 40 N, wherein the sponge is of such a size that it can pass through a trocar having a diameter of around 30 mm, wherein the inter-organ spacer is configured such that it is inserted into the body of a patient through the trocar or an incision, and such that the entire inter-organ spacer is placed in the body during surgery so that no part of the inter-organ spacer occupies the trocar or the incision, and wherein no terminal end of the x-ray contrast agent terminates outside of the sponge.

2. The inter-organ spacer according to claim 1, wherein the porous soft material is polyurethane.

3. The inter-organ spacer according to claim 1, wherein the porous soft material is soft polyurethane foam.

4. The inter-organ spacer according to claim 1, wherein the liquid releasing ability is 80% to 100%.

5. An endoscopic surgery kit, comprising the inter-organ spacer for use in endoscopic surgery according to claim 1, and an insertion device for inserting the inter-organ spacer into a body, said insertion device comprising a tubular holder capable of holding the inter-organ spacer.

6. The endoscopic surgery kit according to claim 5, wherein the insertion device further comprises an introducer that is capable of being inserted from one end of the tubular holder and is capable of ejecting the inter-organ spacer in the tubular holder from another end of the tubular holder.

7. The endoscopic surgery kit according to claim 5, wherein the insertion device further comprises an extractor that is capable of pulling the inter-organ spacer into the tubular holder.

8. The endoscopic surgery kit according to claim 5, wherein the insertion device further comprises a funnel portion capable of being provided at one end of the tubular holder.

9. The inter-organ spacer according to claim 1, wherein the liquid releasing ability is 60% to 100%.

10. The inter-organ spacer according to claim 1, wherein the porous soft material exhibits an ability to indirectly absorb liquid.

* * * * *